United States Patent [19]
Stearns et al.

[11] Patent Number: 5,767,683
[45] Date of Patent: Jun. 16, 1998

[54] SYSTEM FOR DETECTING COMPOUNDS IN A GASEOUS SAMPLE USING PHOTOIONIZATION, ELECTRON CAPTURE DETECTION, AND A CONSTANT CURRENT FEEDBACK CONTROL CIRCUIT WHICH RESPONDS TO COMPOUND CONCENTRATION

[76] Inventors: Stanley D. Stearns, P.O. Box 55603, Houston, Tex. 77255; Huamin Cai, 8850 Chimney Rock, Apt. 68, Houston, Tex. 77096; Wayne E. Wentworth, P.O. Box 55603, Houston, Tex. 77255

[21] Appl. No.: 686,578

[22] Filed: Jul. 26, 1996

[51] Int. Cl.$^6$ .................. G01N 27/62; G01N 27/68
[52] U.S. Cl. .................. 324/464; 324/449; 324/123; 73/28.02
[58] Field of Search .................. 324/449, 450, 324/455, 464, 123, 71.4; 73/28.02, 23.35; 436/153; 313/231.41, 231.71; 315/111.01, 111.91; 250/379, 385.2

[56] References Cited

U.S. PATENT DOCUMENTS

| | | | |
|---|---|---|---|
| 3,540,851 | 11/1970 | Vree et al. | 324/464 X |
| 3,679,973 | 7/1972 | Smith, Jr. et al. | 324/464 X |
| 4,724,394 | 2/1988 | Langer et al. | 324/464 X |
| 4,851,683 | 7/1989 | Yang et al. | 250/339 |
| 5,153,519 | 10/1992 | Wentworth et al. | 324/464 |
| 5,317,271 | 5/1994 | Wentworth et al. | 324/464 |
| 5,394,090 | 2/1995 | Wentworth et al. | 324/464 |
| 5,394,091 | 2/1995 | Wentworth et al. | 324/464 |
| 5,394,092 | 2/1995 | Wentworth et al. | 324/464 |
| 5,528,150 | 6/1996 | Wentworth et al. | 324/464 |
| 5,532,599 | 7/1996 | Wentworth et al. | 324/464 |
| 5,541,519 | 7/1996 | Wentworth et al. | 324/464 |

OTHER PUBLICATIONS

Aue, Walter A.; Siu, K. W. Michael; Anal. Chem Aug. 1980, 52, 1544–1546.
Siu, K. W. Michael; Roper, Christopher m.; Ramaley, louis, Aue, Walter A.,: J. Chromatogr.; 1981, 210, 401–407 (month unavailable).

Primary Examiner—Maura K. Regan
Attorney, Agent, or Firm—Gunn & Associates P.C.

[57] ABSTRACT

A detection system measures very small concentrations of compounds of interest within gaseous samples. A spark discharge system induces pulsed spark discharges across a pair of electrodes within an inert gas in a gas flow chamber. Various reactions are induced by spark interaction with the flow of inert gas, and with any sample or dopant commingled with the inert gas, in the region of the pulsed spark discharge. This induces photon ionization which creates an instantaneous current flow within the gas flow chamber. Current flow is held constant for all concentrations of sample introduced into the gas flow by means of a control feedback system. The output of the control feedback system is indicative of sample concentration. The system responds linearly over approximately five orders of magnitude of sample concentration for use with the sample which will be described and low femtogram sensitivity is achieved.

28 Claims, 2 Drawing Sheets

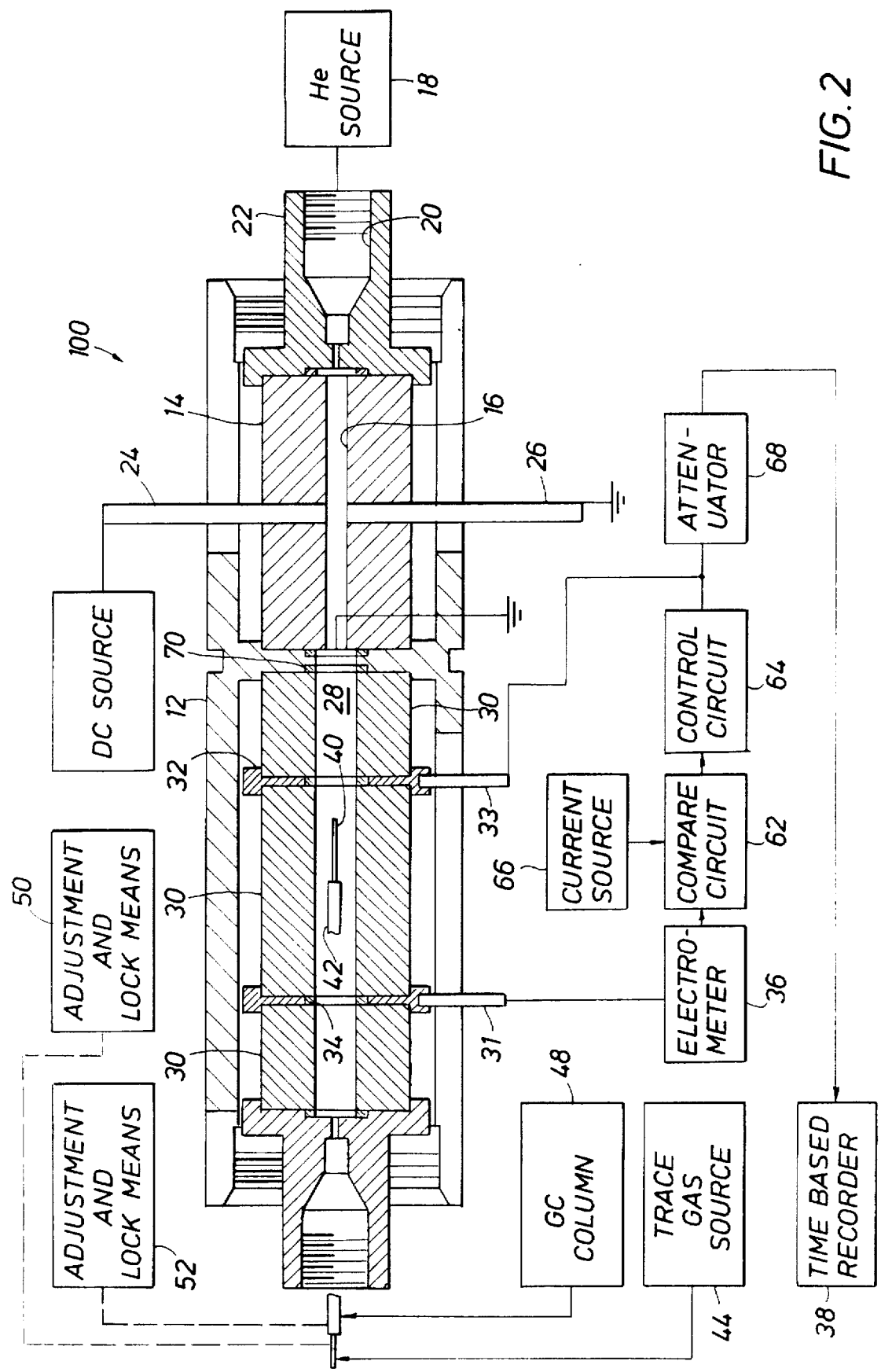

SYSTEM FOR DETECTING COMPOUNDS IN A GASEOUS SAMPLE USING PHOTOIONIZATION, ELECTRON CAPTURE DETECTION, AND A CONSTANT CURRENT FEEDBACK CONTROL CIRCUIT WHICH RESPONDS TO COMPOUND CONCENTRATION

BACKGROUND OF THE INVENTION

1. Field of the Invention

This present disclosure is directed to a spark discharge system for measuring concentrations of gaseous sample, and more particularly directed toward a system measures sample concentration by means of sample ionization and electron capture. Sample ionization created by spark interaction with a flow of an inert gas, helium being the preferred gas stream, in the region of the pulsed spark discharge. This creates the photon ionization for use with the sample which will be described.

2. Background of the Art

U.S. Pat. No. 5,394,090, which is assigned to the assignee of the present disclosure, discloses an electron capture detector (ECD hereinafter) which utilizes a helium flow through a region of the spark discharge. This helium flow is the only flowing material in the immediate region of the spark. Dopant gas and sample gas are injected and commingled with the helium gas downstream from the spark. The dopant gas and sample gas are not exposed directly to the spark discharge thereby reducing the noise level and increasing the life expectancy of the spark electrodes as discussed in the reference. A detector chamber is constructed so that the helium flow continues within the chamber past the spark discharge and through a central axial passage of the chamber having a first, second and third ring shaped electrodes so that the flow is able to interact with the sample gas and the dopant gas. The dopant gas interacts with photon ionization emission from the spark to create a net current flow (via electrons or charged gas molecules as will be explained) within the chamber. This establishes a current flow between two of the electrodes which can be detected by an electrometer connected having an input electrode. This current flow defines the baseline current flow or baseline "signal" of the ECD. In the ECD disclosed in U.S. Pat. No. 5,394,090, the baseline is adjusted by changing the flow rate of the dopant, by changing the point at which the dopant is introduced within the detector chamber, or by also changing the point at which the sample gas and the dopant are introduced into the chamber with respect to the measuring electrodes. The baseline condition or baseline current, established from flows without sample gas, is a selected or established current flow for the referenced detector. When sample is introduced, the referenced ECD response is linear over approximately two orders of magnitude.

The improved ECD of this disclosure enhances the basic detector chamber disclosed in U.S. Pat. No. 5,394,090 by detection circuitry which comprises a bias voltage feedback system. Two versions will be discussed, the first having three electrodes and the second providing a simpler and less costly version. More specifically, the chamber of the first version comprises three electrodes which will be referred to as a collector electrode, a first bias electrode, and a second bias electrode. Turning now to the feedback system, output from an electrometer connected to the collector electrode is compared with a reference current using a comparison circuit. Output from the comparison circuit is input to a control circuit which, in turn, outputs a bias voltage. This bias voltage is applied to the first bias electrode such that the electron current flow within the detector chamber remains constant for all concentrations of input sample gas. The instantaneous setting of the control circuit is used to form a second output. The magnitude of this second output is proportional to the concentration of a selected sample gas within the ECD chamber and is, therefore, the response signal of the disclosed ECD system. Response is linear over approximately five orders of magnitude. The range of linear response represents a significant improvement over the ECD device disclosed in U.S. Pat. No. 5,394,090.

As a test instrument, the ECD is provided with an input gas discharged from a gas chromatograph (GC) column or other suitable source.

The GC column effluent normally carries with it a carrier gas which is routinely input at a specified flow rate. In addition to that, the GC carrier gas delivers in timed sequence peaks of constituents in a tested sample. For instance, in testing the output of any typical petrochemical product, manufactured in large volume, analysis of the purity of the produced product is desirable. One mode of testing is to utilize the GC column which elutes the various constituents in a specific timed sequence dependent on the relative mobility as the sample constituents travel through the GC column. A typical GC column comprises a mobile phase and a stationary phase. The mobile phase comprises a carrier gas such as helium into which sample gas containing one or more compounds is injected. The stationary phase comprises one or more solid constituents within the GC column which exhibit different retention times for the "unknown" sample compounds. The sample gas containing the unknown compounds is injected over a relatively short period of time into the carrier gas flow near the input of the GC column. Sample compounds are retained for different times by the stationary phase of the GC, and then subsequently released. Upon release, each type of sample compound is swept by the carrier gas from the GC column and discharged in the form of a "peak" or maxima in concentration by the carrier gas. Retention times, and therefore time separation of the unknown compound peaks, is a function of several factors including the carrier gas flow rate and the type of the stationary phase within the GC column. The result of an injection near the input of a sample gas containing multiple compounds results in the subsequent release, or "eluetes", of maxima or peak concentrations of individual compounds at the output of the GC column. Again, time recording of the GC output reflects these elutes as peaks. Stated another way, the GC separates sample compounds by eluting in the form of concentration maxima or peaks in the output carrier gas at varying times, measured from the injection of the composite sample gas. As described, the GC process does not quantify the concentrations of the unknown compounds, but does separate multiple compounds for further analysis using the current ECD invention. By using a series of calibration gases, a fixed flow rate, and a specific stationary phase material, the GC process can be used to identify compound types based upon the time position of the eluted peaks, measured with respect to the injection of the composite gaseous sample. There may be any number of eluted peaks formed by the GC column output which peaks must be detected and quantified. The ECD system is a good technique for peak quantification. Enhanced sensitivity is therefore obtained as the peaks of the sample are passed through the ECD device.

Adjustment of an ECD is somewhat delicate. The present disclosure sets forth an arrangement which can be readily adjusted. In this particular version, the ECD forms a base line current as a result of ionization of helium flowing through the pulsed spark discharge. That creates radiation via helium emission sufficient to ionize an introduced dopant located strictly in an isolated region downstream from the spark creating electrodes. The electrodes forming the spark are isolated in an atmosphere of pure helium and therefore create little noise and have an extended life. Dopant gas introduced downstream in the system is input at such a low flow rate that they are swept away from the pulsed spark terminals. Moreover, this assures that the pulsed discharge interacts only with the inert helium, not with the dopant or any samples from the GC column. This prevents burning of any compound which might create soot or otherwise form an undesired deposit on the interior of the ECD equipment. Two concentrically positioned tubes are introduced into the ECD equipment. They are inserted into the flowing stream of helium gas which sweeps the area where the spark is formed. In routine operation, the helium flow is typically in the range of about 20 or more milliliters per minute. A typical flow is about 30 milliliters per minute. This flow enables the insertion of two concentrically located tubes downstream which introduce additional flow but which gases cannot migrate against the larger helium flow which is significantly larger, perhaps 5 to 50 times larger in volume. One injection tube which is positioned in the ECD chamber delivers a trace or dopant gas. It is a gas which is readily ionized and which interacts with the photons from the spark discharge. One example of the dopant gas introduced is methane. It interacts readily and is highly mobile, diffusing in the region downstream from the point of introduction. A second tube is utilized to inject an additional flow downstream. The second tube is located so that its discharge is into the dopant gas diffused area so that the GC column effluent is introduced. The GC column effluent includes the GC carrier gas and the time separated gas (es) as separated peaks from the GC column. Because the separated peaks capture electrons and become negative ions, they cause a current flow variation within the detector chamber from the current flow established under quiescent or baseline conditions. The comparison circuit immediately detects this variation by comparing electrometer and reference currents and sends the appropriate signal to the control circuit which, in turn, adjusts the bias voltage of the first bias electrode so that the internal chamber current returns to baseline conditions. An increase in bias voltage is proportional to the concentration of compound of interest from the GC column. It is apparent, therefore, that a steady state condition must first be established comprising internal chamber current flow and bias electrode voltage for "zero" sample concentration at a given dopant flow rate and dopant injection point. This occurs when a specified flow rate of the dopant gas is introduced. An example might be an introduction rate of 1 milliliter per minute of methane which is introduced into a flow of 30 milliliters per minute of helium. The discharge from the GC column typically will be something of the same magnitude, perhaps a fraction up to about 2 or 3 milliliters per minute. This is introduced downstream of the dopant introduction point.

If the dopant is methane (a relatively mobile molecule), then interaction is readily obtained because the methane will diffuse easily through the flowing stream of helium. The dopant flow in the quiescent state establishes a current flow which is scaled to a maximum value. Thereafter, when a peak is separated by the GC column, the peak constituents delivered to the ECD cause a drop in internal current proportioned to peak quantity. This current drop is sensed by the comparison circuit in a comparison of electrometer and reference currents. The output of the compare circuit is input to the control circuit. The first output of the control circuit adjusts the bias voltage of the first bias electrode so as to restore the chamber current to the baseline value. The second output of the control circuit is indicative of the concentration of peak constituents. As will be understood in the detailed description of current flow in the following paragraph, the peak amplitude tends to create an instantaneous and proportionate current flow decrease.

Helium ions and free electrons are created when the preferred helium gas flow is exposed to the spark creating electrodes through the reaction:

$$He=He^{+}+e^{-}$$

where $He^+$ denotes a positively charged helium ion and $e^-$ denotes a free electron. Helium is usually a diatomic molecule. The mechanisms by which it is converted include a change in molecular charge and also excitation to a metastable state. The metastable state is achieved by transition of an orbiting electron to a higher energy state, and then return to the lower energy state. The return to the lower energy state forms an output photon which has a frequency related to the energy loss. Both mechanisms may occur in the helium; thus, the helium flows through the spark and is excited to form $He_2^+$ and $He^*$. After the spark, some of the energy from the free electron flux interacts with neutral helium in the flow. This interaction forms $He_2^+$ and excited helium $He^+$ through the reactions:

$$e^{-}+He=He^{-}+e^{-},$$

and $$He^{+}+He=He_2^{+} \qquad (2)$$

Subsequently, the helium decays by the emission of a photon through reactions such as:

$$He^{*}=He+hv \text{ (unspecified energy level)},$$

and $$He_2^{+}+e^{-}=2He+hv \text{ (about 11 to 21 eV)}. \qquad (3)$$

The dominant mechanism appears to be decay of the diatomic helium ions. As dopant gas is introduced into the chamber, the photons produced by the reaction of Equation (3) interact with the dopant to produce D ions and free electrons through the reaction:

$$hv+D=D^{+}+e^{-} \qquad (4)$$

The flow of dopant ions and free electrons establishes the previously Refined base line current of the device. Once an "unknown" compound, denoted generically as "AB", is introduced into the system, the free electrons of Equation (4) can initiate several classes of reactions and examples including:

$$e^{-}+AB=(AB)^{-} \qquad (5)$$

After introduction of the unknown compound AB, the unknown competes for some of the electron population defining the steady state or base line conditions. As a result, the introduction of a compound AB results in an observed current flow drop in the ECD system.

Summarizing, the present ECD system utilizes the spark formed across a pair of terminals transverse to the helium flow introduced into the system. Radiation resultant from the photon ionization of the helium creates an interaction downstream with an introduced dopant in small volume. This establishes a current rate which is the steady state condition for the ECD and which is held constant by a feedback system. Downstream of the dopant introduction point, another introduction point is used to inject the GC column eluted peaks along the GC column carrier. The first, second and third terminals are utilized having the preferred form of encircling rings about the passage, and an output of the feedback system is indicative of the combinations of compounds of interest in the GC elute electrometer output. The output signal is typically recorded by a time based recorder, and is linear over approximately five orders of magnitude.

BRIEF DESCRIPTION OF THE DRAWINGS

So that the manner in which the above cited features, advantages and objects of the present invention are obtained and can be understood in detail, more particular description of the invention, briefly summarized above, may be had by reference to the embodiments thereof which are illustrated in the appended drawings. It is to be noted, however, that the appended drawings illustrate only typical embodiments of the invention and are therefore not to be considered limiting of its scope for the invention may admit to other equally effective embodiments.

FIG. 2 shows a simplified version of the device.

DETAILED DESCRIPTION OF THE PREFERRED EMBODIMENT

Figure 1:
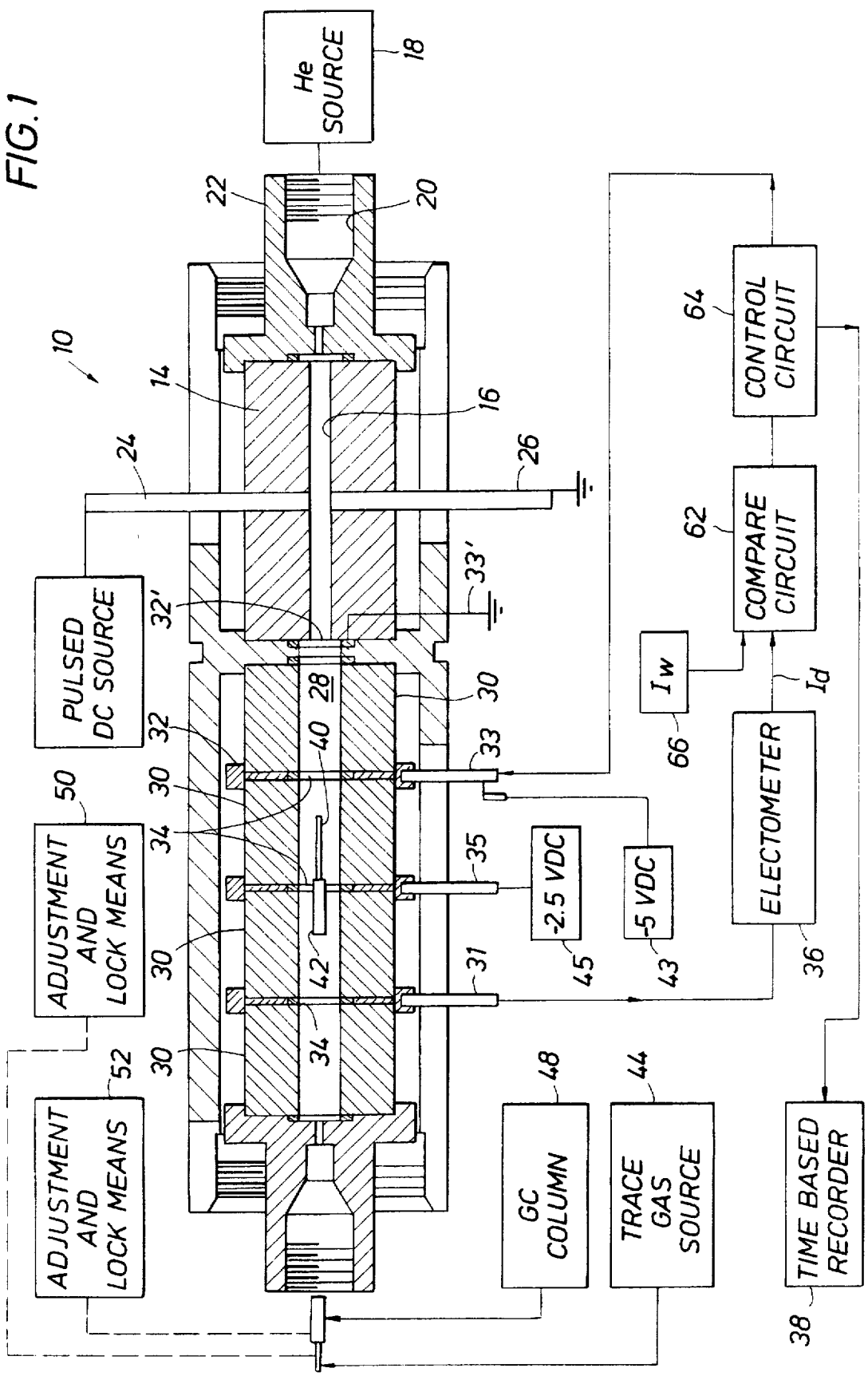
FIG. 1 shows, in section, the internal workings of the ECD of the present disclosure illustrating a helium gas input cooperative with a pair of spaced electrodes and further having a reaction chamber downstream equipped with three circular, ring shaped electrodes and further includes a dopant injection tube and a GC column effluent injection tube located for operation in the ECD with the feedback circuit.

Attention is directed to FIG. 1 where the numeral 10 identifies the ECD system of this disclosure. The description of FIG. 1 will be given first and then FIG. 2 will be detailed. It is constructed with an elongate cylindrical housing 12 which contains a cylindrical member 14 which is axially hollow at 16. This forms a passage through which helium is introduced. Helium is the preferred form of gas although other inert gases are known to be applicable. The helium flows from a regulated helium source 18 which is connected through a regulator (not shown) to deliver helium at a pressure slightly above atmospheric pressure and flowing at a rate of 20 about 20 to about 150 milliliters per minute. This flow is introduced into an industry standard fitting detail 20 formed in a fitting body 22 at one end of the equipment. By means of a suitable externally threaded nut (not shown), the fitting body 22 is held in the illustrated position to assure locking in the ECD apparatus 10. Flow is directed, from the fitting 22 into the passage 16. The flow is directed to the axial passage 16 and moves between a pair of spaced electrodes. The electrodes are identified at 24 and 26. They preferably terminate in parallel end faces. More specifically, the parallel end faces are constructed on metal rods having a diameter of about 1/16" and which are spaced with end faces approximately 1/16" across the passage 16. In an optional aspect of this particular embodiment, the electrodes are reduced in diameter to a smaller diameter of about 0.3 mm. This can be obtained by forming the two electrodes 24 and 26 of wire stock of that size. In an alternate aspect, larger electrodes can be used and sharpened points can be formed with that size. As before, it is desirable that the points be located so that the spark is transverse to the gas flow in the passage 16. The two terminals which form the spark define a sharply fixed, narrowly constrained spark on each spark formation so that the spark does not dance around the two electrode faces, and remains in the form of a straight line. Consequently, it is not necessary to otherwise confine the spark location. It is also not necessary to include any sort of light collimation mechanism. Rather, the light is collimated because the spark definition is relatively narrow and constrained.

Again referring to FIG. 1, the flow passage 16 connects downstream with a larger passage 28. The passage 28 is formed on the interior of a spacer rings 30 which are preferably sapphire insulators. Several spacer rings 30 are positioned serially to define the extended passage 28 through which the helium flows. In the preferred embodiment, there are several spacer rings separated by three identical electrode rings 32, and a ground electrode ring 32' connects to a ground 33'. The electrode rings are provided with an external encircling collar which includes an inwardly directed webbing connecting with the exposed electrode rings 34. The rings 34 located in the passage 28 and are flush mounted with the passage. They are formed of metal and has an exposed face which is defined by the spacing by adjacent rings 30. Moreover, the rings 34 cooperate with connectors extending through the ECD chamber thereby forming a collector electrode 31, a first bias electrode 33, and a second bias electrode 35 for operation of the ECD. The first bias electrode 33 is connected with a negative voltage source 43 and is typically biased negatively in the range of about 5 to about 20 volts direct current (VDC). As illustrated, approximately −5 VDC will suffice for operation. The next bias electrode 35 is connected with a bias voltage source 45; a selected bias is about −2.5 VDC.

The remaining non-grounded ring and electrode 31 serves as a collector electrode for the ECD and provides a connector terminal for an electrometer 36 which measures current flow within the chamber 10 induced initially by a spark discharge across the electrodes 24 and 26. Specifics reactions which produce this current flow will be discussed in detail in a subsequent section.

The system also includes first and second injection tubes as shown in the view. In the preferred embodiment, they are arranged concentric of each other and are positioned axially in the structure. The smaller tube 40 introduces a fixed flow rate of a trace gas or "dopant". It is provided by the trace gas source 44. The second of the two concentric tubes 42 is also an input conduit to the ECD chamber and introduces a flow from a GC column 48. This flow is introduced at a different location. Stated another way, the two injection tubes 40 and 42 terminate at different locations within the flow passage 28. This changes the introduction region, making it adjustable for reasons to be described. The tubes 40 and 42 are moved back and forth with respect to the body of the ECD 10. For this purpose, the tube 40 is moved to a selected or adjustable position and a lock means 50 is then operated to fix the terminus of the tube 40 at a specified location within the flow passage 28. In similar fashion, a lock means 52 is used to lock the terminus of the tube 42 at a specified location within the flow passage 28. As shown in the drawings, arrows indicate relative movement of the tubes 40 and 42. In the concentric deployment of the two tubes, there is sufficient flow space in the two tubes to introduce the desired gas flow rate for operation of the equipment. If desired, the tubes can be positioned adjacent to each other and introduce the two gas flows through immediately adjacent small capillary tubes. In another aspect of construction, the tubes can be fixedly located by extending through the spacer rings 30 to position a discharge point approximately at the centerline axis of the flow passage 28. Adjustments however are thought to be advantageous and for that reason, the tubes 40 and 42 are inserted coaxially of the ECD structure which makes it relatively easy to move the tubes left and right as viewed in the drawings.

Referring still to the drawing, the gas flow from the helium source 18 which is introduced into the system moves from right to left within the passages 16 and 28. It is substantially greater than the gas flow from the tubes 40 and 42. Therefore the dopant gas and GC column effluent are simply swept along the larger volume of helium in this system. The tube 40 introduces the dopant which is forced to the left by the larger helium flow volume and the dopant gas diffuses in this region. It is available for interaction with the photon ionization from the spark gap. It is one theory of operation of the present system that the photon ionization is created by the transitory existence of spark created diatomic helium molecules which quickly breakdown into single atoms of the inert gas. In this transition a photon of light energy within a relatively broad spectrum is emitted and directed along the passage way 16 and in the chamber 28. By testing with an inserted opaque shutter, the transmission can be stopped which seems to completely stop the photon ionization with the dopant gas. Restated, it appears that light transmission must be obtained so that the photons emitted from the spark region are able to interact with the dopant gas. It is desirable that the dopant gas therefore be within view of the spark. So to speak, the view must be something of a straight line or alternately must include sufficient reflective surfaces to direct the photon ionization emission to the region at which dopant is introduced. In the illustrated construction, no particular reflective materials are required, although sapphire is preferred as an insulating material 30. So to speak, a light tunnel is defined by the passages 16 and 28, and the light from the spark gap formed by the electrodes 24 and 26 is not able to diffuse through the bodies which form the passage structure. The light is therefore directed along the passage 16 and into the flow passage 28.

The physical spacing from the spark gap at the electrodes to the regions of the rings 34, associated first bias electrode 33, the second bias electrode 35, and the collector electrode 31 is not overly long. Distances of up to about 2 or 3 centimeters have been effectively used. Accordingly, a smaller ECD construction can be used. This is a scale of ECD which is quite effective. If for instance, the chamber 28 is excessively broad, small peaks eluted from the GC column will simply be lost as the peaks diffuse excessively laterally. Therefore the diameter of the chamber 28 is preferably reduced. As the diameter is reduced and the length is reduced, sensitivity to the smaller peaks is enhanced. Sensitivity is also enhanced by proper positioning of the tip of the two injection tubes 40 and 42. The tube 40 is moved to introduce the dopant gas approximately even with the ring of the first bias electrode 33. The second tube 42 terminates approximately even with the ring of the second bias electrode 35. This enables the electric field established by the first and second bias electrodes 33 and 35 to interact with the dopant gas and also the eluted peak gases from the GC column to have space to interact with the drifting electrons as the gases are swept to the left of FIG. 1. A steady state current is established with a particular flow rate of dopant gas from the injection tube 40. That is adjusted so that a maximum value is established. This adjustment can be changed by changing the flow rate of the dopant gas, by moving the location of the injection tube 40 with respect to the first and second electrodes, and by changing the velocity of the helium gas through the system. Spacing of the electrodes can also make a difference in this aspect. Since, however, the electrodes are structurally fixed in location, for a given construction of ECD, adjustments are more readily made by moving the tube 40 or by changing the flow rate of the helium through the system. In any case, a specified base line of current is established, recalling that this is a maximum current flow.

When a sample compound of interest is introduced into the flow passage 28 by means of the sample injection tube 42, a portion of the free electron population tends to interact with a compound within the sample denoted again in general as compound AB. Typical reactions utilized in the operation of the ECD are expressed mathematically in equations (5) and (6). As a result of these reactions, the instantaneous current within the chamber tends to drop. Stated another way, reactions expressed by equations (5) and (6) remove some of the electron population initially established under "zero" sample baseline conditions. The electrometer 36, which is connected to the collector electrode 31, measures the instantaneous current flow $I_d$ and outputs this current to the comparison circuit 62. A reference current $I_w$, which is generated at source 66 and preferably equals the chamber current. $I_w$ under quiescent or baseline conditions, is also input into the comparison circuit 62. The circuit 62 establishes a null or base current which continues until a sample compound AB is input. This defines the initial condition. The comparison circuit 62 outputs a signal to the control circuit 64 which is proportion to the instantaneous difference between the currents $I_d$ and $I_w$. The control circuit outputs a first signal which adjusts the bias voltage of bias electrode 33 such that the current $I_w$ within the chamber is returned to the constant, baseline value. The change in bias voltage is added to the initial bias level (some DC voltage in the representative set up) so that the electrode 33 voltage is modified dynamically. The amount of adjustment is a linear function of the concentration of sample compound within the flow passage 28. The amount of adjustment is output from the control circuit 64 in the form of a second output, which is directly proportional to sample concentration. This second output is preferably recorded as a function of time using a time based recorder 38.

It should be recalled that the instant current flow within the chamber passage 28 decreases as sample concentration increases. Therefore, for given sample and dopant injection points, and for given helium, dopant, and GC effluent flow rates, instantaneous $I_w$ will vary inversely with the magnitude of the concentration of the specified sample compound AB. In order to maintain a constant current flow within the ECD chamber, the bias voltage of the first bias electrode 33 must be made more negative by the control circuit 64.

It should also be restated that the second output of the control circuit is proportional to the sample concentration. In order to record measured sample concentrations in absolute units, such as picograms, the ECD system must be calibrated. For calibration, a controlled quantity of eluted sample gas containing a known concentration of compound AB is introduced through the tube 42. This mimics a peak which is separated by the conventional operation of the GC column. This separated peak is permitted to pass through the system. When peak passage occurs, it interacts with electrons in the flowing helium carrier gas associated from the ionized dopant gas to change the second output of the control circuit 64 which is input to the time based recorder 38. The second output of the control circuit 64 is initially in arbitrary units. Since, however, the concentration of compound AB is known, the second output of the control circuit 64 can be rescaled or "calibrated" to read concentrations of AB in absolute measurements. Subsequent concentration measurements of the compound AB can, therefore, be recorded with the time based recorder 38 in absolute units, such as picograms.

In regular operation of this equipment the two tubes may be moved to a particular location and locked in location. Alternately, the two tubes can be adjusted from time to time depending on the system requirements. As a generalization, system operations remain substantially unaltered even though there may be variations in the pulse rate for the pulsed DC source which is connected to the terminal 24. Moreover, it is operated to form serial isolated, individual DC pulses. The various pulses are delivered at a control rate typically in the range of 10–10,000 individual pulses per second. The duty cycle is preferably one in which very narrow pulses are formed without ringing. Narrow pulses typically are preferred having a pulse width of perhaps 10 microseconds or less. The voltage is sufficient to cause breakdown and therefor formation of the visible spark.

ALTERNATE EMBODIMENT

FIG. 2 discloses an alternate embodiment to the structure shown in FIG. 1. FIG. 2 is a simplified construction and is therefore less costly to manufacture. In addition, it provides good performance with fewer adjustments. The electrode system is simplified as will be seen at a glance. In this regard, the electrometer 36 remains connected to the same electrode as shown in FIG. 1. It is connected with the compare circuit 62 and control circuit 64 as before. The circuit 64 is connected to provide a bias on the input 33. This bias is permitted to fluctuate over a wide range and therefore enables operation over a greater dynamic range. As illustrated, the control circuit 64 responds to the two input signals from the electrometer 36 and the current source 66. It therefore provides the necessary feedback signal. This tends to restore the current flow of the ECD. The output signal of the control circuit is therefore used to maintain the set current flow through the ECD. The control circuit output is also provided to the recorder 38. Typically, this involves an intermediate attenuator 68.

As a convenience to the system, the cabinet or housing can be formed of metal and grounded, but it is probably more desirable to directly ground the rings 70 which surround the passage 28.

The embodiment of FIG. 2 illustrates that the system will work either with a pulsed DC source or a steady state DC source. As before, the spark acts on the helium to provide the excitation which is used in the ECD downstream. The excitation as noted before involves a number of reactions. In one, the diatomic molecule is charged or ionized. This will create an effective current flow through the ECD. In addition, the diatomic molecule may be excited by momentarily causing an orbital electron to move to a higher energy state. That state is maintained for a fraction of a second at which time the electron will surrender the photon of energy necessary to enable the electron to return to a lower energy state. This emits a photon of energy which is formed by the transition from a particular higher energy state back to the lower energy state. This forms a characteristic emission band for the diatomic molecule. Without regard to the particular mechanism, the excited helium gas interacts with the dopant and the GC provided sample to quantify the excursion of current flow which is ultimately recorded. In this particular instance, rather than recording the voltage measured by the electrometer 36, the recorded signal is in fact the current flow provided for the electrode which adjusts the operating conditions in the system. The feedback signal is therefore the signal of interest.

While the foregoing is directed to the preferred embodiment, the scope is determined by the claims which follow.

We claim:

1. A gas detector comprising:
   (a) an elongate gas flow chamber for receiving a gas sample therein;
   (b) a set of electrodes exposed to a gas flow containing said gas sample in said chamber, wherein said set of electrodes comprises
      (i) a collector electrode which measures a flow of current induced within said gas sample by means of an electrical discharge, and
      (ii) at least one bias electrode which controls said flow of current;
   (c) means providing a gas flow in said chamber to carry said gas sample by said set of electrodes;
   (d) an electrometer connected to said collector electrode; and
   (e) a feedback loop connected to said electrometer and to a first bias electrode of said at least one said bias electrode, wherein said feedback loop
      (i) maintains a constant flow of said current within said chamber and
      (ii) produces an output proportional to a concentration of said gas sample.

2. The apparatus of claim 1 wherein said feedback loop comprises a comparison circuit having a fixed input thereto and an input from said electrometer to form a control signal.

3. The apparatus of claim 2 wherein said control signal is connected by means of a control circuit to said first bias electrode thereby maintaining said constant current flow in said chamber.

4. The apparatus of claim 3 wherein said feedback loop is connected to a time base recorder to record signals from said feedback loop indicative of said concentration of sample gas.

5. The apparatus of claim 4 wherein bias voltage is applied by said control circuit to said first bias electrode of said electrode set, and wherein said first bias electrode is positioned in said gas flow chamber upstream from said collector electrode to interact with the gas flow therein and thereby control said current flow.

6. The apparatus of claim 5 wherein said set of electrodes comprises said first bias electrode, and a second bias electrode to which a constant potential is applied, and wherein said first and second bias electrodes are circular surfaces around said gas flow chamber and gas sample flows through said circular surfaces.

7. The apparatus of claim 1 wherein said gas flow chamber includes a carrier gas inlet directing flow along said gas flow chamber toward a carrier gas output and the flow of carrier gas therein moves past said at least one bias electrode of said electrode set.

8. The apparatus of claim 7 including a sample gas inlet input into said flow of said carrier gas in said chamber, wherein the sample gas inlet directs the sample gas past said at least one bias electrode in said gas flow chamber.

9. The apparatus of claim 8 wherein said feedback loop is connected to a first bias electrode to control the flow of electrical charge in said gas flow.

10. The apparatus of claim 9 wherein a voltage at said first bias electrode is recorded to form an output signal indicative of said concentration of gas sample within said gas flowing through said chamber.

11. A method of operating an electron capture detector to measure and quantify a sample AB flowing therethrough with a carrier gas flow, comprising the steps of:

(a) flowing a carrier gas through a test chamber between an input and output;

(b) creating electrons, by means of an electrical discharge, in the carrier gas to flow along the test chamber;

(c) directing the gas flow past a measuring electrode to form a signal indicative of number of electrons at the measuring electrode;

(d) injecting the AB sample into the test chamber to decrease the measuring electrode signal from a baseline value by an amount dependent on the concentration of AB sample; and (e) forming a feedback signal based upon the magnitude of the measuring electrode signal, where said feedback signal
   (i) is used to restore the measuring electrode signal to said baseline value, and
   (ii) is used to measure and quantify the AB sample.

12. The method of claim 11 wherein said feedback signal is formed by:

(a) providing said measuring electrode signal to a comparison circuit;

(b) providing a set point input to said comparison circuit; and (c) operating said comparison circuit dependent on the set point and measuring electrode signal thereby providing said feedback signal.

13. The method of claim 12 wherein the amount said electrode signal deviates from said baseline value is directly proportional to the concentration of AB.

14. The method of claim 12 wherein the step of forming the feedback signal includes the additional steps of:

(a) positioning said measuring electrode downstream from said electrical discharge in said test chamber;

(b) measuring a charge current in said chamber at said measuring electrode;

(c) applying the measured value as a signal input to said comparison circuit; and (d) forming an output signal at the comparison circuit and applying the output signal to a bias electrode in said chamber, such that said bias electrode returns said measuring electrode signal to said baseline value.

15. The method of claim 14 wherein the step of applying a signal to said bias electrode changes the electron flow in the test chamber in the carrier gas from a quiescent current flow.

16. The method of claim 15 further including the step of defining the quiescent current flow at a specified maximum value and wherein the AB sample flowing therein causes a decrease from that maximum current flow, and measuring the decrease to indicate the quantity of the AB sample.

17. The method of claim 16 further including the step of forming the electrons in the carrier gas by forming said electrical discharge in the carrier gas flow upstream of the injection of the AB sample.

18. The method of claim 17 wherein said electrical discharge liberates electrons in the carrier gas flow, and the carrier gas flow and electrons flowing therewith move along the test chamber toward an output of said chamber and first past said bias electrode and then past said measuring electrode, both positioned within said chamber.

19. The method of claim 11 wherein electrons are liberated in the carrier gas from an upstream location within said test chamber and the electrons flow with the gas flow along said test chamber to define a quiescent current flow therein.

20. A gas detector comprising:

(a) an elongate chamber for flowing a gas sample therethrough;

(b) a set of electrodes in said chamber exposed to a gas sample flow wherein said set of electrodes comprises:
   (i) a collector electrode which provides a flow of current induced within said gas sample by an electrical discharge, and
   (ii) a bias electrode to control said current flow;

(c) a sample gas source providing a gas flow in said chamber to carry said gas sample by said set of electrodes; and (d) a feedback loop which cooperates with said collector electrode and said bias electrode, wherein said feedback loop
   (i) maintains a constant flow within said chamber and
   (ii) produces an output proportional to said sample concentration.

21. The apparatus of claim 20 wherein said feedback loop comprises a comparison circuit having a fixed input thereto and an input from said electrometer to form a control signal.

22. The apparatus of claim 21 wherein said control signal is connected by a control circuit to said bias electrode to control said constant current flow in said chamber.

23. The apparatus of claim 22 wherein bias voltage is applied by said control circuit to said bias electrode of said electrode set, and wherein said bias electrode is positioned in said gas flow chamber upstream from said collector electrode to interact with the gas flow therein and thereby control said current.

24. The apparatus of claim 20 wherein said gas flow chamber includes a carrier gas inlet directing flow along said gas flow chamber toward a carrier gas output and the flow of carrier gas therein moves past said at least one bias electrode of said electrode set.

25. A method of operating an electron capture detector to measure and quantify a sample AB flowing therethrough with a carrier gas flow, comprising the steps of:

(a) flowing a carrier gas through a test chamber between an input and output;

(b) creating electrons, mixing in the carrier gas to flow along the test chamber;

(c) directing the gas flow past a measuring electrode to form a signal indicative of electrons flowing to at the measuring electrode;

(d) injecting the AB sample into the test chamber to vary the measuring electrode signal from a baseline value by an amount dependent on the concentration of AB sample; and (e) forming a feedback signal based upon the magnitude of the measuring electrode signal, where said feedback signal
   (i) restores the measuring electrode signal to said baseline value, and
   (ii) measures the AB sample.

26. The method of claim 25 wherein said feedback signal is formed by:

(a) providing said measuring electrode signal to a comparison circuit;

(b) providing a set input to said comparison circuit; and (c) operating said comparison circuit dependent on the set input and measuring electrode signal thereby providing said feedback signal.

27. The method of claim 26 wherein the electrode signal deviates from said baseline value is related to the concentration of AB.

28. The method of claim 26 wherein the step of forming the feedback signal includes the additional steps of:

(a) positioning said measuring electrode downstream from said electrical discharge in said test chamber;

(b) measuring a charge current in said chamber at said measuring electrode;

(c) applying the measured value as a signal input to said comparison circuit; and (d) forming an output signal at the comparison circuit and applying the output signal to a bias electrode in said chamber, such that said bias electrode returns said measuring electrode signal to said baseline value.

* * * * *